(12) United States Patent
Gotzen

(10) Patent No.: US 6,203,544 B1
(45) Date of Patent: Mar. 20, 2001

(54) FIXATION ELEMENT

(75) Inventor: Leo Gotzen, Marburg (DE)

(73) Assignee: Tutogen Medical, Inc., Parsipanny, NJ (US)

( * ) Notice: Subject to any disclaimer, the term of this patent is extended or adjusted under 35 U.S.C. 154(b) by 0 days.

(21) Appl. No.: 09/195,324

(22) Filed: Nov. 18, 1998

(30) Foreign Application Priority Data

Nov. 19, 1997 (DE) ............................................. 197 51 284

(51) Int. Cl.⁷ .................................................. A61B 17/86
(52) U.S. Cl. ................ 606/72; 606/73; 606/96; 606/104
(58) Field of Search .................. 606/53, 59, 60, 606/61, 62, 65, 67, 69, 72, 73, 75, 76, 77, 96, 104; 623/16

(56) References Cited

U.S. PATENT DOCUMENTS

| | | | |
|---|---|---|---|
| 4,781,182 | * 11/1988 | Purnell et al. | 606/96 |
| 5,122,132 | * 6/1992 | Bremer | 606/72 |
| 5,868,749 | * 2/1999 | Reed | 606/76 |

FOREIGN PATENT DOCUMENTS

| | | |
|---|---|---|
| 29 06 650 C2 | 5/1989 | (DE) . |
| 40 04 941 A1 | 8/1990 | (DE) . |
| 39 23 411 A1 | 1/1991 | (DE) . |
| 42 05 118 C1 | 6/1994 | (DE) . |
| 43 00 039 C1 | 9/1994 | (DE) . |
| 44 06 374 A1 | 9/1994 | (DE) . |
| 195 04 955 A1 | 8/1996 | (DE) . |
| 0 674 880 A1 | 3/1995 | (EP) . |
| WO 97/25945 | 7/1997 | (WO) . |
| WO 97/37603 | 10/1997 | (WO) . |

OTHER PUBLICATIONS

Albee, Fred H., Bone Graft Surgery in Disease, Injury and Deformity, D. Appleton–Century Company, New York, 1940: pp. 216, 217 and 220, 1940.*

Habal and Reddi, Bone Grafts & Bone Substitutes, W.B. Saunders Company, Philadelphia, et al. 1992: Chapters 2–3, pp. 6–10.

* cited by examiner

Primary Examiner—David O. Reip
(74) Attorney, Agent, or Firm—Fitch, Even, Tabin & Flannery

(57) ABSTRACT

The fixation element for osteosynthesis in a human or animal body consists of cortical bone matter which is conserved and sterilized. A section with a reduced cross-section is provided in the region of the forward end of the fixation element.

16 Claims, 1 Drawing Sheet

FIXATION ELEMENT

BACKGROUND OF THE INVENTION

The invention relates to a fixation element for osteosynthesis in the human or animal body. Fixation elements of this kind are known in principle and serve to fixate bone fragments, e.g. in distal radius fractures. In this it is known in the framework of the so-called bore wire osteosynthesis to stabilise distal radius fractures with Kirschner's wire, which is however disadvantageous in a number of regards. On the one hand, infections can arise after the insertion of these metallic wires. On the other hand, metal allergies can arise. Finally, a second operation is always required after the healing of the fracture in which the metallic elements are removed.

Furthermore, it is known to use fixation elements of plastic which are absorbed in the body for the fixation of fractures. To a high percentage, however, plastic elements of this kind lead to foreign-body reactions and osteolyses. In addition their bending strength decreases very strongly in a period of time of about 2–3 weeks so that the stability required for the bone healing is not sufficiently ensured.

SUMMARY OF THE INVENTION

The problem (object) lying at the basis of the invention is to provide a fixation element of the initially named kind by means of which a stable and lasting fixing of bone fragments can be achieved and in which a second operation for the removal of foreign bodies can be dispensed with.

The satisfaction of this object takes place through the features of claim 1 and in particular in that the fixation element consists of cortical bone matter which is conserved and sterilised. In accordance with the invention a fixation element of cortical bone is inserted which has a lower strength per se than a Kirschner's wire. It has however proved that it is sufficient to use a weaker material than metal for the fixation of bone fragments, with the advantages resulting in the use of fixation implants of cortical bone matter that foreign-body reactions are eliminated, no metal allergies can arise and a second operation for the removal of the foreign body can be dispensed with. Through this the total costs of the healing process are greatly reduced, with the dangers connected with an additional narcosis or a second operation also being eliminated.

The fixation element in accordance with the invention is anchored in the bone fragments, through which the osteosynthesis becomes more stable than in the use of absorbable plastic pins. In addition the cortical bone matter is transformed into the body's own bone matter so that an optimal healing of the fracture can be achieved.

In accordance with the invention cortical fixation elements can be used which are produced from allogenic or xenogenic bone matter.

Advantageous embodiments of the invention are described in the description, the figures and the subordinate claims.

In accordance with a first advantageous embodiment the fixation element can be designed as a screw or a nail. Embodiments of this kind of fixation elements are admittedly known in principle, but lead to particular advantages in conjunction with the material in accordance with the invention, however.

In accordance with a further embodiment of the invention a section with a reduced cross-section can be provided in the region of the front end of the pin or the nail with a reduced cross-section. Through this there results the great advantage that the fixation element can be anchored in a bore at the opposite corticalis of the radius bone, with it not being possible for the main body of the fixation element to slip through this bore, which leads to a very stable connection.

The transition to the section with reduced cross-section preferably extends conically, with an angle of about 45° to the longitudinal axis of the fixation element having proved particularly advantageous in order to achieve a fixed anchoring in the opposite corticalis.

It is advantageous when the cross-section of the contracted section amounts to about 80 to 85% of the cross-section of the remaining fixation element, preferably between about 3 and 5 $mm^2$.

The contracted section can extend over about 10 to 20% of the total length of the fixation element, preferably over about 10 mm. Such a length is sufficient in order to ensure a good and firm anchoring in the opposite corticalis.

In accordance with a further exemplary embodiment of the invention the fixation element is designed as a screw and preferably has placement surfaces for a wrench. Screws of this kind are admittedly known in principle as fixation elements, but the initially mentioned advantages result through the use of cortical bone matter.

In the screw-like fixation element it is particularly advantageous when the transition between the screw head and the screw body extends conically, through which a collar is formed, which is supported on the bone fragment to be fixated. The collar permits the projecting screw head to be sawed off in the event that this is necessary.

A setting tool in accordance with the invention for pin-shaped fixation elements has two sleeve-like guides, which can be fixed relative to one another at a selectable acute angle. Through this the fixation element in accordance with the invention can be used more readily in different planes and at different angles with the help of the fixing wire. Through the guides, which are adjustable relative to one another, the size of the angle between the guide wire, which is inserted through one of the sleeves, and the fixation element to be inserted, which is held by the other guide, can easily be adjusted.

BRIEF DESCRIPTION OF THE DRAWING

The following invention will be described in the following in a purely exemplary manner with reference to advantageous embodiments and with reference to the accompanying drawings. Shown are.

DESCRIPTION

Figure 1:
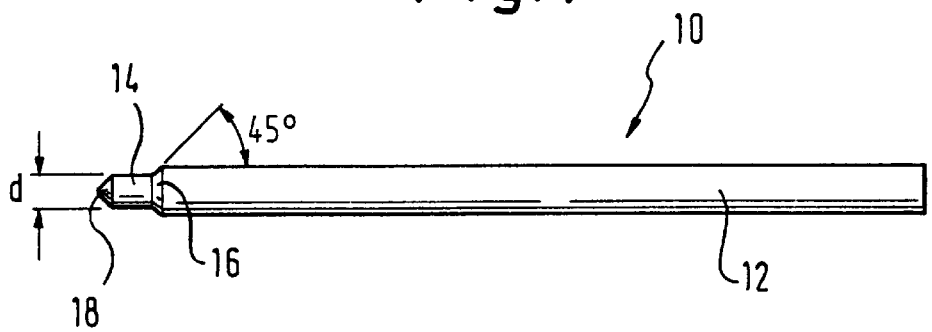
FIG. 1 a side view of a fixation element which is executed as a pin.

The fixation element 10 shown in FIG. 1 is executed in the manner of a pin and serves for osteosynthesis in a human or animal body. The fixation element is produced from cortical bone matter which is conserved and sterilised. The fixation element 10 has a main body 12 with cylindrical cross-section, at the forward end of which a section 14 with a reduced cross-section is provided. The transition 16 between the main body 12 and the section with a reduced cross-section extends conically at an angle of about 45° to the longitudinal axis of the fixation pin.

The apex 18 of the fixation pin 10 is conically sharpened at an angle of 45°. Thus the contracted section 14 is located between the conical apex 18 and the conical transition region 16.

The cross-section of the section 14 amounts to about 80 to 85% of the cross-section of the main body 12. In the illustrated exemplary embodiment the diameter d of the contracted section 14 amounts to 2.5 mm, whereas the diameter of the main body 12 amounts to 3 mm. The total length of the fixation pin 10 amounts to 60 mm, with the axial length from the forward tip to the end of the transition region 16 amounting to 10 mm.

In a further (non-illustrated) embodiment the diameter of the main body 12 amounts to 2.5 mm and the diameter of the contracted section amounts to 2.0 mm. In both embodiments the fixation pin is designed to have a circular cross-section.

Figure 2:
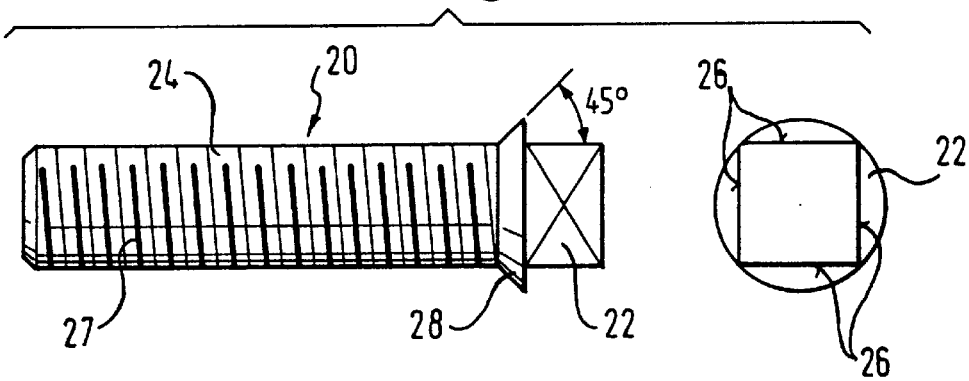
FIG. 2 a cross-sectional view and a plan view of a screw-like fixation element.

FIG. 2 shows a further embodiment of a fixation element in the form of a screw 20 which has a screw head 22 and a screw body 24. Application surfaces 26 for a wrench are provided at the screw head 22. The screw body 24 has a Whitworth thread 27 and is sharpened or pointed at its front end. In this both the screw body 24 and the screw head 22 are designed cylindrically.

The transition between the screw head 22 and the screw body 24 extends conically at an angle of 45° in the fixation screw 20 illustrated in FIG. 2, through which a support surface in the form of a collar 28 is formed. In particular when the protruding screw head 22 is sawed off after the insertion of the fixation screw 20, this collar 28 serves for the support on the bone fragment to be fixed.

The total length of the fixation screw 20 illustrated in FIG. 2 amounts to 24 mm, with the length of the screw body 24 amounting to 20 mm. The screw length and diameter can however be varied.

Figure 3:
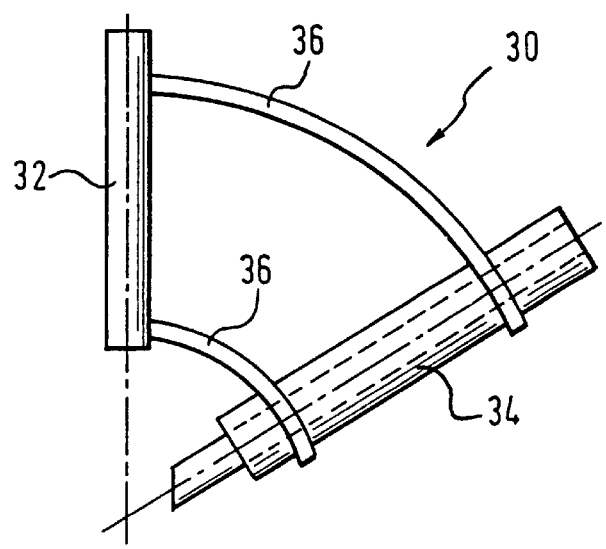
FIG. 3 a side view of a setting tool.

FIG. 3 shows a setting tool 30 for fixation pins which has two sleeve-like guides 32 and 34 which can be fixed relative to one another at a selectable acute angle via curved tracks 36. In this the guide 32 serves or the insertion of a guide wire and the guide 34 for the insertion of the fixation element.

For the insertion of the fixation pin 10 illustrated in FIG. 1 a corresponding bore hole is made after a fragment repositioning, with the boring tool serving at the same time as a guide wire for the setting tool 30, which is placed onto the latter. The setting tool is guided up to the bone through a stab incision and fixated. A bore hole is made at the radius bone through the guide 34 for the fixation pin 10 in such a manner that a bore is present in the contracorticalis with a diameter which corresponds to the contracted end 14. Then the fixation pin 10 is laid into the guide 34 of the setting tool 30 and inserted with a tamping tool and a hammer. Then the setting tool 30 can be removed.

For the insertion of the fixation screw 20 illustrated in FIG. 2, after the production of the usual operative access and the repositioning of the fragments, a draw hole is bored which is provided with a thread. After a sliding hole boring up to the fracture gap and the turning in of the screw with a wrench which is provided for this—in the event that this required—the protruding screw head is sawed off, with the collar 28 then serving as a fixation surface for the bone fragment.

In a non-illustrated exemplary embodiment of the invention a nail in the form of a round bone pin which is sharpened at one end and has a flat head at the other end is provided as a fixation element. A nail of this kind serves for the fixation of osteochondral fragments and for the fixation of small bone fragments in various fractures.

The fixation screw illustrated in FIG. 2 serves for the osteosynthesis for example in a caput radii fracture, in basal fractures of the fifth metatarsal bone, in scaphoid bone fractures, in inner malleolus fractures, in accompanying minimal osteosyntheses, in the use of a fixateur externe, in patella fractures which are not subjected to tensile stress, in tuberculum majus fractures and in other indications.

In contrast to bone ceramics in which organic materials as well as collagen are burned, the fixation elements of cortical bone matter in accordance with the invention have both minerals and collagens, which significantly accelerates the healing process. Although fixation elements of cortical bones are weaker than metallic implants, they are sufficiently stable for the fragment fixation for many fractures. In accordance with the invention it has proved that materials of this kind bring about significant advantages as a result of the improved compatibility, in particular since a second operation for the removal of foreign bodies can be dispensed with. A method can be used for the production and conservation of the bone matter in accordance with the invention such as is described in DE 29 06 650 C2, to which reference is expressly made here.

What is claimed is:

1. Fixation element for osteosynthesis in a human or animal body, comprising a main body of cortical bone matter which is conserved and sterilised, and in the form of a pin or a nail, the main body including forward and rearward ends with a longitudinal axis extending therebetween and having a section of uniform diameter with a reduced cross-section at or adjacent the forward end wherein the section extends over about 10–20% of the total length of the fixation element.

2. Fixation element in accordance with claim 1, wherein the main body includes a transition to the section extending conically relative to the longitudinal axis.

3. Fixation element in accordance with claim 1, wherein the forward end is conically sharpened.

4. Fixation element in accordance with claim 3, wherein the section adjoins at the conically sharpened end.

5. Fixation element in accordance with claim 1, wherein the main body has a circular cross-section.

6. Setting tool for a fixation element in accordance with claim 1, wherein the setting tool has two sleeve-like guides which can be fixed with respect to one another at a selectable acute angle.

7. Setting tool for a fixation element in accordance with claim 1, wherein the setting tool has two sleeve-like guides which can be fixed with respect to one another at a selectable acute angle.

8. A fixation element for osteosynthesis in a human or animal body, said fixation element having the shape of a pin or nail and comprising a main body with a forward end and with a rearward end and a longitudinal axis extending therebetween, at said forward end a section with a reduced cross-section being provided which is followed by a conically sharpened apex, a transition between said main body and said section with a reduced cross-section amounting to about 80–85% of the cross-section of the remaining fixation element, wherein said fixation element consists of cortical bone matter which is conserved and sterilised.

9. A fixation element in accordance with claim 8, wherein the transition to the section extends at an angle of about 45° to the longitudinal axis.

10. A fixation element in accordance with claim 8, wherein the cross-section of the remaining fixation element amounts to between about 3 and 5 mm$^2$.

11. Fixation element in accordance with claim 8, wherein the section extends over about 10 mm.

12. Fixation element in accordance with claim 8, wherein said fixation element is designed with a circular cross-section.

13. Fixation element for osteosynthesis in a human or animal body, said fixation element having the shape of a screw and comprising a screw body and a screw head, a transition between said screw body and said screw head extending conically and forming a support surface in the form of a collar, wherein said fixation element consists of cortical bone matter which is conserved and sterilised.

14. Fixation element in accordance with claim 13, wherein application surfaces for a wrench are provided on the screw head.

15. Fixation element in accordance with claim 14 wherein the screw head and the collar are of different predetermined configurations such that the screw head extends axially for a distance greater than the collar so that the screw head projects for being severed from the collar after setting the fixation element in the body.

16. Fixation element in accordance with claim 13, wherein the transition between the screw head and the screw body extends at about 45°.

\* \* \* \* \*